United States Patent [19]

Uchikuga et al.

[11] 4,413,129
[45] Nov. 1, 1983

[54] PROCESS FOR PREPARING THE $H_2$-RECEPTOR ANTAGONIST CIMETIDINE

[75] Inventors: Saburo Uchikuga, Yokohama; Tomoyasu Tashiro, Hatano; Yasuko Osawa, Tokyo, all of Japan

[73] Assignee: Sogo Pharmaceutical Company, Ltd., Kanagawa, Japan

[21] Appl. No.: 113,135

[22] Filed: Jan. 17, 1980

Related U.S. Application Data

[62] Division of Ser. No. 38,265, May 11, 1979, abandoned.

[30] Foreign Application Priority Data

Dec. 27, 1978 [JP] Japan ............................. 53-159895

[51] Int. Cl.³ ........................................... C07D 233/64
[52] U.S. Cl. ................................................. 548/342
[58] Field of Search ............................................ 548/342

[56] References Cited

U.S. PATENT DOCUMENTS

| | | | |
|---|---|---|---|
| 3,897,444 | 7/1975 | Durant et al. | 548/342 X |
| 3,950,333 | 4/1976 | Durant et al. | 548/342 X |
| 3,979,398 | 9/1976 | White | 548/342 X |
| 4,048,319 | 9/1977 | Black et al. | 548/342 X |

FOREIGN PATENT DOCUMENTS 1338169  3/1972  United Kingdom ................ 548/342

OTHER PUBLICATIONS

Ball, D., et al., *J. Org. Chem.*, 28, 1589 (1963).
Kice, J., et al., *J. Am. Chem. Soc.*, 88, 5245 (1966).
Klayman, D., et al., *Quart. Reports on Sulfur Chem.*, 3 (3), 191 and 231–232 (1968).

*Primary Examiner*—Richard A. Schwartz
*Attorney, Agent, or Firm*—Browdy and Neimark

[57] ABSTRACT

Cimetidine, namely N-cyano-N'-methyl-N"-[2-((4-methyl-5-imidazolyl) methylthio) ethyl] guanidine which is useful as an antagonist of $H_2$-receptor is prepared by reacting 4-methyl-5-[(2-aminoethyl) thiomethyl] imidazole, which is obtained by the reaction of 4-methyl-5-hydroxymethylimidazole on 2-aminoethanethiolsulfuric acid, with O-alkyl-S-alkyl-cyanothioimidocarbonate to give N-cyano-N'-[2-((4-methyl-5-imidazolyl) methylthio) ethyl]-O-alkylisourea, which is reacted with monomethylamine. According to the present process, cimetidine can be prepared in good yield and desired purity with very reduced amount of methyl mercaptan released from the reaction.

2 Claims, No Drawings

PROCESS FOR PREPARING THE H₂-RECEPTOR ANTAGONIST CIMETIDINE

This is a division, of application Ser. No. 38,265 filed May 11, 1979, now abandoned.

This invention relates to a novel method for preparing cimetidine.

Cimetidine is a compound represented by the following formula (VII):

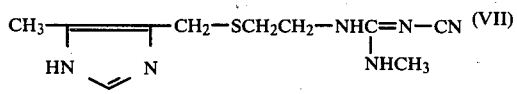

namely, N-cyano-N'-methyl-N''-[2-((4-methyl-5-imidazolyl)methylthio)ethyl]guanidine, and it is a histamine H₂-receptor antagonist which depresses specifically the gastric acid secretion caused by histamine stimulation, therefore it is useful as an anti-ulcer agent and ulcer-treating agent and has been already commercially available.

Hitherto, cimetidine has been prepared according to the method comprising the following three steps of:

(i) reacting 4-methyl-5-hydroxymethylimidazole with cysteamine;

(ii) reacting dialkyl-cyanamidedithiocarbonate, especially dimethyl-ester thereof (dimethyl-cyanodithioimidocarbonate), therewith and then (iii) reacting monomethylamine therewith to yield cimetidine.

However, the prior method above described for the synthesis of cimetidine has many important and fatal drawbacks as follows: unstability of starting material; difficulty of producing it; long period requirement for the synthesis of cimetidine due to low-reactivity of the starting material; strict process control; environment pollution problems caused by release of a large amount of alkyl mercaptan, especially methyl mercaptan; decrease of yield and purity of cimetidine caused by side reaction and so forth.

The present invention comprises, for removing at once many drawbacks of the prior method above described, the reaction steps as follows:

reacting 4-methyl-5-[(2-aminoethyl)thiomethyl]imidazole of the formula (III)

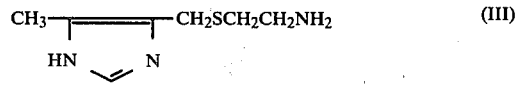

with O-alkyl-S-alkyl-ester of cyanamidethiocarbonic acid (O-alkyl-S-alkyl-cyanothioimidocarbonate) corresponding to the formula (IV)

(wherein $R_1$ is lower alkyl and
$R_2$ is alkyl of one to ten carbon atoms.)
to yield N-cyano-N'-[2-((4-methyl-5-imidazolyl)-methylthio)ethyl]-O-alkylisourea of the formula (V)

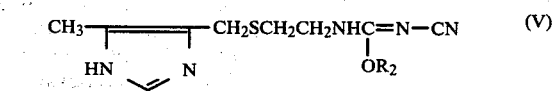

(wherein $R_2$ has the same meaning as in the formula above)
and,
reacting the N-cyano-O-alkylisourea derivative thus obtained with monomethylamine of the formula (VI)

$$CH_3NH_2 \qquad (VI)$$

to form the desired product cimetidine corresponding to the formula (VII).

As described above, the significant characteristic of this invention lies in novel discovery of possibility of using O-alkyl-S-alkyl-ester of the formula (IV).

That is to say, according to the prior method, as obvious from the step (ii), it is necessary to use S-dialkyl-ester of cyanamidedithiocarbonic acid (for example, especially dimethyl ester) [dialkyl (for example, especially dimethyl) cyanodithioimidocarbonate] corresponding to the following formula (IV').

(R is alkyl.)

Since this carbonate (IV') contains two RS-groups (especially CH₃S-groups) in one molecule, during the reactions with amines according to the steps (ii) and (iii) described above, 2 moles of alkyl mercaptan, especially methyl mercaptan, a powerfully odorous material, are released resulting in a powerful stink and resultant air pollution. Methyl mercaptan is a source of stink pollution and air pollution, and therefore a release of such a pollutant in large quantities has comprised an extremely serious drawback.

On the contrary, according to the method of the present invention, O-alkyl-S-alkyl-ester of cyanamide-thiocarbonic acid (O-alkyl-S-alkyl-cyanothioimidocarbonate) of the formula (IV) is used as described above. This ester (IV) does not contain two RS-groups but only one RO-group and one RS-group, therefore, when reacting said ester (IV) with the amine (III), the reaction with RS-group is selectively effected to release only one mole of alkyl mercaptan, and then, when reacting with monomethylamine (VI), the reaction with RO-group is selectively effected, thereby producing the desired compound of cimetidine while being accompanied with producing the by-product alcohol.

That is to say, according to the present method, since only one mole of alkyl mercaptan is released from one mole of O-alkyl-S-alkyl-ester of cyanamidethiocarbonic acid (O-alkyl-S-alkyl-cyanothioimidocarbonate) (IV), the present invention has an extremely great pollution preventing effect. Moreover, although, in accordance with the prior method, S-dialkyl ester of cyanamidedithiocarbonic acid (dialkyl-cyanodithioimidocarbonate) must be synthesized by reacting one mole of di-alkali metal salt of cyanodithioimidocarbonic acid with two moles of alkylating agent, O-alkyl-S-alkyl ester of cyanamidethiocarbonic acid (O-alkyl-S-alkyl-cyanothioimidocarbonate) employed in the present invention can be synthesized by reacting one mole of mono-alkali metal salt of O-alkyl-cyanothioimidocarbonic acid with only one mole of alkylating agent of which amount corresponds to half of that used in the prior method above described. Namely, the present invention has a great effect that it is quite enough to employ only a half amount of alkylating agent as compared with the prior method.

And furthermore, as different from the step (iii) of the prior method, according to the present invention, the reaction of methylamine on RO-group of the isourea derivative (V) is carried out extremely specifically and highly selectively with scarcely any side reaction. As a result, there is a great effect that large quantities of cimetidine can be prepared in good yield and desired high purity. And also, said ester (IV) can be obtained very easily by the reaction of cyanamide with alkali metal alkyl xanthate known as a flotation agent, so that it is available very easily and also it is a stable compound which is advantageously easily used.

Furthermore, the present invention has also the following feature as well as those described above: namely, its significant characteristic lies in that it is the 2-aminoethanethiolsulfuric acid of the formula (II)

$$HO_3S-S-CH_2CH_2-NH_2 \qquad (II)$$

that is selectively used as the substance to be reacted with 4-methyl-5-hydroxymethylimidazole of the formula (I). In the prior method, as obvious from the step (i) above described, cysteamine has been used as said substance.

Thus, according to the method of the present invention, wherein 2-aminoethanethiolsulfuric acid (II) is used, as against the prior art method wherein cysteamine is used, the reaction is completed in one short hour, so that it is not necessary at all to be heated at reflux for a long period of ten hours; that is to say, according to the present method, there is an extremely great processing advantage in that the time required for the process can be reduced to 1/10, in other words, the reaction can be conducted tenfold as rapidly as in the prior method. The advantage associated with this 2-aminoethanethiolsulfuric acid is that since it can be easily obtained from ethyleneimine and thiosulfate and it is extremely stable, it is not necessary at all to pay special attention to treatment thereof, as well as that said 2-aminoethanethiolsulfuricacid has a high reactivity as described above.

Moreover, while in the use of cysteamine of the prior method, it is indispensable to carry out the reaction in an air-free atmosphere for example in a nitrogen stream in order to prevent oxidation, the present method never requires such condition and therefore it is really an epoch-making invention.

It is a novel organic chemical reaction having been not yet reported in any literatures to form thioether linkage by reacting -OH group of 4-methyl-5-hydroxymethylimidazole (I) with -S.SO$_3$H group of 2-aminoethanethiolsulfuric acid (II).

According to the process of the present invention, 4-methyl-5-hydroxymethylimidazole (I), in the form of salts such as mineral acid salts or free bases, may be reacted with 2-aminoethanethiolsulfuric acid (II). In this process, these starting materials are heated at reflux in acetic acid or hydrohalogenic acid, or, in such a condition that is mixed with other organic solvent for a period of about one hour. The subsequent reactions can be easily effected in the conventional organic solvents, water or mixed solvents, preferably in the alcoholic solvents (ethanol, isopropanol and so forth) at about room temperature.

The present invention is a method of producing cimetidine, in good yield and high purity, by the efficient and pollution controlled reaction wherein freely available compounds of 2-aminoethanethiolsulfuric acid and O-alkyl-S-alkyl-ester of cyanamidethiocarbonic acid (O-alkyl-S-alkyl-cyanothioimidocarbonate) are used as novel reactants.

Some specific embodiments of the present invention will now be described in the following Examples.

EXAMPLE 1

(i) 9.0 g of 4-methyl-5-hydroxymethylimidazole hydrochloride and 10.2 g of 2-aminoethanethiolsulfuric acid are heated at reflux for 80 minutes in 50 ml of acetic acid, and the reaction mixture is concentrated, passed through 250 ml of a strongly basic anion exchange resin (trade name: Amberlite IRA-410[OH$^-$]) and eluted with water. The eluate is concentrated under reduced pressure and dried to yield 8.93 g of 4-methyl-5-[(2-aminoethyl)thiomethyl]imidazole as an oily product (yield: 86.2%).

To the oily product above obtained an aqueous solution of ammonium picrate is added, thus formed precipitate is filtered off, and then the precipitate is recrystallized 2 times from water-containing alcohol to obtain picrate thereof. This picrate is analyzed by infrared spectrum and melting point, so that it is found to coincide with the picrate prepared by another method.

m.p.: 176.0°–177° C.

(ii) A solution of 3.6 g of O-ethyl-S-methyl ester of cyanamidethiocarbonic acid in 20 ml of ethanol is added dropwise to 4.3 g of 4-methyl-5-[(2-aminoethyl)thiomethyl]imidazole dissolved in 10 ml of ethanol. The solution is stirred overnight at room temperature, thereafter is concentrated, and then is subjected to a silica gel column chromatography using the solvent system acetone:chloroform:water (300:50:40) to separate a fraction containing reaction product. The separated fraction is concentrated, then crystallized from the solvent system ethanol:water. The resulting crystals are filtered off and dried to yield 4.71 g of N-cyano-N'-[(2-((4-methyl-5-imidazolyl)methylthio)ethyl]-O-ethylisourea as white crystals (yield: 78.3%).

m.p.: 143.0°–145.0° C.

Elemental analysis: C$_{11}$H$_{17}$N$_5$SO

|  | C | H | N | S |
| --- | --- | --- | --- | --- |
| Found (%) | 49.39 | 6.44 | 26.52 | 12.00 |
| Calculated (%) | 49.42 | 6.41 | 26.20 | 11.99 |

(iii) 31 ml of a 40% aqueous solution of monomethylamine is added dropwise with cooling by ice to 2.0 g of N-cyano-N'-[2-((4-methyl-5-imidazolyl)methylthio)ethyl]-O-ethylisourea dissolved in the mixed solvent of 60 ml of water and 45 ml of ethanol. The solution is stirred for one night, thereafter is concentrated under reduced pressure, and then is subjected to a silica gel column chromatography using the solvent system acetone:chloroform:water (300:5:40) to isolate a reaction product, which is then concentrated under reduced pressure. Thus obtained concentrate is crystallized with the aid of isopropyl alcohol-ether to yield 1.52 g of the desired product, cimetidine, namely N-cyano-N'-methyl-N''-[2-((4-methyl-5-imidazolyl)methylthio)ethyl]guanidine (yield: 80.3%). I.R. and m.p. thereof are identical with those of authentic sample.

m.p.: 139.5°–141° C.

Elemental analysis: $C_{10}H_{16}N_6S$

|  | C | H | N | S |
|---|---|---|---|---|
| Found (%) | 47.50 | 6.63 | 33.59 | 12.82 |
| Calculated (%) | 47.60 | 6.39 | 33.30 | 12.71 |

EXAMPLE 2

A ethanolic solution of 4.8 g of O-amyl-S-methyl ester of cyanamidethiocarbonic acid is added to 4.3 g of 4-methyl-5-[(2-aminoethyl)thiomethyl]imidazole, which is prepared according to the method described in Example 1 (i), dissolved in 10 ml of ethanol. The solution is stirred overnight at room temperature, concentrated and then chromatographed in the same manner as in Example 1 (ii) to separate a reaction product. The separated reaction product is concentrated under reduced pressure and then dried to yield 5.6 g of N-cyano-N'-[2-((4-methyl-5-imidazolyl)methylthio)ethyl]-O-amylisourea as an oil (yield: 72.0%).

60 ml of a 30% aqueous solution of monomethylamine is added dropwise with cooling by ice to 5.6 g of above obtained oily product dissolved in the mixed solvent of 30 ml of ethanol and 20 ml of water. After overnight reaction at 0° C., the solution is concentrated under reduced pressure and then chromatographed under the same conditions as those of Example 1 (iii) to fractionate reaction products. Thus a separated solution is concentrated under reduced pressure and then crystallized from isopropyl alcohol-ether to yield 3.3 g of the desired product N-cyano-N'-methyl-N''-[2-((4-methyl-5-imidazolyl)methylthio)ethyl]guanidine (yield: 72.3%).

m.p.: 138.5°–140.5° C.

I.R. and m.p. thereof are identical with those of authentic specimen.

EXAMPLE 3

In the same manner as in Example 1 (i), 2.8 g of 4-methyl-5-hydroxymethylimidazole (free base) is reacted with 4.3 g of 2-aminoethanethiolsulfuric acid, yielding 3.0 g of 4-methyl-5-[(2-aminoethyl)thiomethyl]imidazole as an oily product (yield: 72.0%).

An ethanolic solution of 2.6 g of O-isopropyl-S-methyl ester of cyanamidethiocarbonic acid is added dropwise to 3.0 g of above obtained oily product in solution in 10 ml ethanol. After overnight stirring at room temperature, the solution is concentrated and chromatographed similarly as in Example 1 (ii) to fractionate reaction products. Thus a separated solution is concentrated under reduced pressure and dried, yielding 4.0 g of N-cyano-N'-[2-((4-methyl-5-imidazolyl)methylthio)ethyl]-O-isopropylisourea as an oily product (yield: 77.8%).

50 ml of a 30% aqueous solution of monomethylamine is added dropwise with cooling by ice to 4.0 g of above obtained oily product dissolved in the mixed solvent of 50 ml of ethanol and 50 ml of water. After overnight reaction at 0° C., the solution is concentrated under reduced pressure and chromatographed similarly as in Example 1 (iii) to separate a reaction solution. Thus obtained solution is concentrated under reduced pressure and then crystallized from isopropyl alcohol-ether to yield 2.6 g of cimetidine, namely N-cyano-N'-methyl-N''-[2-((4-methyl-5-imidazolylmethylthio)ethyl]guanidine (yield: 71.4%).

m.p.: 139.5°–141.5° C.

I.R. and m.p. thereof are identical with those of authentic specimen.

EXAMPLE 4

An ethanolic solution of 3.0 g of O-octyl-S-methyl ester of cyanamidethiocarbonic acid is added dropwise to 2.2 g of 4-methyl-5-[(2-aminoethyl)thiomethyl]imidazole, which is prepared by the method such as described in Example 1 (i), in solution in 10 ml ethanol. After overnight stirring at room temperature, the solution is concentrated and subjected to chromatography similarly as in Example 1 (ii) to separate reaction products. The separated reaction solution is concentrated under reduced pressure and dried, yielding 3.2 g of N-cyano-N'-[2-((4-methyl-5-imidazolyl)methylthio)ethyl]-O-octylisourea in the form of oily product (yield: 70.0%).

To 3.2 g of the oily product dissolved in the mixture of 40 ml of ethanol and 30 ml of water, 40 ml of a 30% aqueous solution of monomethylamine is added dropwise with cooling by ice. After reaction at 0° C. overnight, the solution is concentrated under reduced pressure and chromatographed similarly as in Example 1 (iii) to separate a reaction solution. The solution is concentrated under reduced pressure and then crystallized from isopropyl alcohol-ether, yielding 1.7 g of cimetidine, namely N-cyano-N'-methyl-N''-[2-((4-methyl-5-imidazolyl)methylthio)ethyl]guanidine (yield: 73.6%).

m.p.: 139.0°–141.0° C.

I.R. and m.p. thereof is consistent with those of authentic specimen.

EXAMPLE 5

4.8 g of 4-methyl-5-hydroxymethylimidazole sulfate is reacted with 5.2 g of 2-aminoethanethiolsulfuric acid according to the procedure described in Example 1 (i), yielding 3.8 g of 4-methyl-5-[(2-aminoethyl)thiomethyl]imidazole as an oily product (yield: 73.3%).

An ethanolic solution of 3.0 g of O-ethyl-S-methyl ester of cyanamidethiocarbonic acid is added dropwise to 3.8 g of said oily product in solution in 10 ml ethanol. After stirring at room temperature overnight, the solution is concentrated and chromotographed in the same manner as in Example 1 (ii) to isolate a reaction product. Thus separated reaction product is concentrated and crystallized from solvent mixture of ethanol-water. Such one which is formed by this crystallization is separated by filtration and then dried, yielding 4.3 g of N-cyano-N'-[2-((4-methyl-5-imidazolyl)methylthio)ethyl]-O-ethylisourea as a white crystal (yield: 72.7%).

m.p. 143.5°–145.5° C.

90 ml of a 30% aqueous solution of monomethylamine is added dropwise with cooling by ice to 4.3 g of N-cyano-N'-[2-((4-methyl-5-imidazolyl)methylthio)ethyl]-O-ethylisourea dissolved in the mixture of 90 ml of ethanol and 60 ml of water. After reaction at 0° C. overnight, the solution is concentrated under reduced pressure and chromatographed similarly as in Example

What is claimed is:

1. A process for preparing cimetidine comprising
reacting 4-methyl-5-hydroxymethylimidazole in the form of mineral acid salt or free base, with 2-aminoethanethiolsulfuric acid in acetic acid, to obtain 4-methyl-5-[(2-aminoethyl)thiomethyl]imidazole;
reacting said 4-methyl-5-[(2-aminoethyl)thiomethyl]imidazole with O-alkyl-S-alkyl ester of cyanamidethiocarbonic acid to yield N-cyano-N'-[2-((4-methyl-5-imidazolyl)methylthio)ethyl]-O-alkylisourea; and
reacting said N-cyano-N'-[2-((4-methyl-5-imidazolyl)methylthio)ethyl]-O-alkylisourea with monomethylamine, and thereby obtaining cimetidine.

2. A process for preparing 4-methyl-5-[(2-aminoethyl)thiomethyl]imidazole of the formula (III)

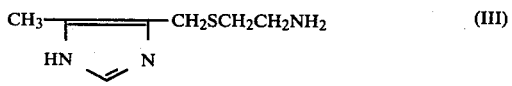

comprising:
reacting in acetic acid 4-methyl-5-hydroxymethylimidazole of the formula (I) in the form of mineral acid salt or free base

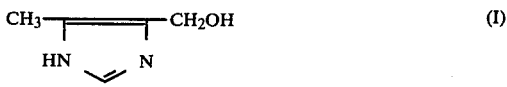

with 2-aminoethanethiolsulfuric acid of the formula (II)